(12) United States Patent
Miles et al.

(10) Patent No.: US 9,166,358 B2
(45) Date of Patent: Oct. 20, 2015

(54) SYSTEMS AND METHODS FOR LASING FROM A MOLECULAR GAS

(75) Inventors: Richard B. Miles, Princeton, NJ (US); Arthur Dogariu, Hamilton, NJ (US); James B. Michael, Ames, IA (US)

(73) Assignee: Trustees of Princeton University, Princeton, NJ (US)

( * ) Notice: Subject to any disclaimer, the term of this patent is extended or adjusted under 35 U.S.C. 154(b) by 197 days.

(21) Appl. No.: 13/546,888

(22) Filed: Jul. 11, 2012

(65) Prior Publication Data

US 2014/0064316 A1 Mar. 6, 2014

Related U.S. Application Data

(60) Provisional application No. 61/506,477, filed on Jul. 11, 2011, provisional application No. 61/511,424, filed on Jul. 25, 2011.

(51) Int. Cl.
| | |
|---|---|
| *H01S 3/097* | (2006.01) |
| *G01N 21/17* | (2006.01) |
| *H01S 3/094* | (2006.01) |
| *H01S 3/22* | (2006.01) |
| *G01N 21/65* | (2006.01) |

(Continued)

(52) U.S. Cl.
CPC .......... *H01S 3/097* (2013.01); *G01N 21/1717* (2013.01); *G01N 21/65* (2013.01); *H01S 3/094092* (2013.01); *H01S 3/22* (2013.01); *G01N 2021/1725* (2013.01); *G01N 2021/1793* (2013.01); *G01N 2021/655* (2013.01); *H01S 3/0014* (2013.01); *H01S 3/2391* (2013.01)

(58) Field of Classification Search
CPC .......... H01S 3/22; H01S 3/94; H01S 3/0014; H01S 3/094092; H01S 3/097; H01S 3/2391
USPC ........................................ 372/55, 70
See application file for complete search history.

(56) References Cited

U.S. PATENT DOCUMENTS 4,318,060 A * 3/1982 Davis ............................. 372/70
2007/0146716 A1 6/2007 Dudelzak et al.

OTHER PUBLICATIONS

Goldsmith, "Two-photon laser-induced fluorescence and stimulated emission measurements from oxygen atoms in a hydrogen/oxygen flame with pico second resolution", 1987, Applied Optics, vol. 26, No. 17, pp. 3566-3572.*

(Continued)

*Primary Examiner* — Yuanda Zhang
*Assistant Examiner* — Michael Carter
(74) *Attorney, Agent, or Firm* — MH2 Technology Law Group, LLP

(57) ABSTRACT

Systems and methods for lasing molecular gases, and systems and methods of detecting molecular species are provided. The systems and methods can include the use of an excitation laser tuned to a wavelength associated with oxygen or nitrogen. The lasing can occur in both the forward and reverse directions relative to the excitation laser beam. Reverse lasing can provide a laser beam that propagates back toward the excitation laser source, and can provide a method for remote sampling of molecular species contained in the air. For example, systems and methods of detecting a molecular species of interest can be achieved by using the properties of the backward or forward propagating air laser to indicate a change in a pulse from the source of laser pulses caused by a modulation laser tuned to interact with the molecular species of interest.

37 Claims, 13 Drawing Sheets

(51) Int. Cl.
 *H01S 3/00* (2006.01)
 *H01S 3/23* (2006.01)

(56) References Cited

OTHER PUBLICATIONS

Dogariu, "High gain backward lasing in air", Jan. 28, 2011, Science, 28.*
Dogariu, Arthur et al. Remote air lasing for trace detection. Proceedings of SPIE, vol. 8024 May 13, 2011, pp. 80240H-1-80240H8.
Alden, Marcus et al. Two-photon-excited stimulated emission from atomic oxygen in flames and cold gases. Optic Letters, Mar. 15, 1989, vol. 14, No. 6, pp. 305-307.
Agrup, Sara et al. Two-photon laser-induced flourescence and stimulated emission measurements from oxygen atoms in a hydrogen/oxygen flame with picosecond resolution. Optics Communications, Dec. 15, 1994, vol. 113, No. 1-3, pp. 315-323.
Bianconi, Sandrine. PCT Invitation to Pay Additional Fees and Partial International Search Report from International Application No. PCT/US2012/046305 dated Dec. 3, 2012, 5 Pages.
International Search Report and Written Opinion dated Apr. 19, 2013, International Application No. PCT/US2012/046305, filed Jul. 11, 2012, pp. 1-22.
Hemmer, Philip R. et al., Standoff spectroscopy via remote generation of a backward-propagating laser beam, PNAS, Feb. 4, 2011, vol. 108, No. 8, pp. 3130-3134.

* cited by examiner

SYSTEMS AND METHODS FOR LASING FROM A MOLECULAR GAS

PRIORITY

This application claims the benefit of priority from U.S. Provisional Application No. 61/506,477, filed Jul. 11, 2011, which is herein incorporated by reference in its entirety; and also claims the benefit of priority from U.S. Provisional Application No. 61/511,424, filed Jul. 25, 2011, which is also herein incorporated by reference in its entirety.

STATEMENT REGARDING FEDERALLY SPONSORED RESEARCH OR DEVELOPMENT

This invention was made with U.S. Government support under Grant No. N00014-09-1-1065 awarded by the Office of Naval Research. The U.S. Government has certain rights in the invention.

FIELD

This disclosure relates to systems and methods directed to lasing from a molecular gas and optoelectronics and remote detection.

SUMMARY

In one aspect, the present disclosure is directed to a method for lasing of a molecular gas. The method for lasing can include using a source of laser pulses to dissociate at least one molecular species comprising atomic constituents into the atomic constituents. The method can also include using the source of laser pulses to excite at least one of the dissociated atomic constituents into an upper electronic state by at least two-photon absorption, where the excited atomic constituent is configured for amplified stimulated emission of radiation from the upper electronic state, the emission of radiation being directed in both a backward direction and a forward direction relative to the laser.

In one aspect, the present disclosure is directed to a method of detecting molecular species in air. The method for detecting molecular species in air can include using a source of laser pulses to dissociate at least one molecular species comprising atomic constituents into the atomic constituents. The method can also include using the source of laser pulses to excite at least one of the dissociated atomic constituents into an upper electronic state by at least two-photon absorption, where the excited atomic constituent is configured for amplified stimulated emission of radiation from the upper electronic state, the emission of radiation being directed in both a forward direction and in a reverse direction along an excitation laser path, leading to air laser beams propagating in both the forward direction and the reverse direction. Detection can be achieved by using the properties of the backward or forward propagating air laser to indicate a change in a pulse from the source of laser pulses caused by a modulation laser tuned to interact with the molecular species of interest. The method can also include employing stimulated Raman scattering effects where the air laser beams interact with a specific molecular species in the excitation laser path, the interaction producing coherent Raman shifted sidebands comprising wavelengths, where the wavelengths can be indicative of the specific molecular species.

In a further aspect, the present disclosure is directed to an molecular air laser. The air laser can include a source of laser pulses configured to dissociate at least one molecular species comprising atomic constituents into the atomic constituents. The source of laser pulses can further be configured to excite at least one of the dissociated atomic constituents into an upper electronic state by at least two-photon absorption, where the excited atomic constituent is configured for amplified stimulated emission of radiation from the upper electronic state, the emission of radiation being directed in both a backward direction and a forward direction relative to the laser.

In an additional aspect, this disclosure is directed to a method of detecting molecular species in air. The method can include using a source of laser pulses to dissociate at least one molecular species comprising atomic constituents into the atomic constituents and using the source of laser pulses to excite at least one of the dissociated atomic constituents by at least two-photon absorption. In further aspects, the source of laser pulses can be a single laser or a first laser and a second laser. The method can also include using a modulation laser to generate a modulation beam configured to co-propagate with a beam from the source of laser pulses along an excitation laser path, and determining whether the co-propagating modulation beam alters a property of a reverse-propagating air laser beam. Consistent with this aspect, a gain path can be at least in a reverse direction along the excitation laser path, leading to the reverse-propagating air laser beam. Furthermore, the modulation beam can be configured to transfer energy to a specific molecular species such that the energized specific molecular species alters an index of refraction of air in the excitation laser path. In another aspect, the modulation beam can be configured to alter the amplitude of the beam from the second laser through a stimulated Raman interaction, wherein a wavelength of the modulation beam is offset by a wavelength value of a Raman resonance of a specific molecular species from a wavelength of the beam from the second laser.

In a further aspect, this disclosure is directed to a system for detecting molecular species in air. The system can include a source of laser pulses configured to dissociate at least one molecular species comprising atomic constituents into the atomic constituents and configured to excite at least one of the dissociated atomic constituents by at least two-photon absorption. In further aspects, the source of laser pulses can be a single laser, or can be a first laser and a second laser. The system can also include a modulation laser configured to generate a modulation beam, the modulation beam configured to co-propagate with a beam from the source of laser pulses along an excitation laser path. Consistent with this aspect, a gain path can be at least in a reverse direction along the excitation laser path, leading to a reverse-propagating air laser beam. Moreover, consistent with this aspect, the modulation beam can be configured to transfer energy to a specific molecular species such that the energized specific molecular species alters an index of refraction of air in the excitation laser path. In another aspect, the modulation beam can be configured to alter the amplitude of the beam from the second laser through a stimulated Raman interaction, wherein a wavelength of the modulation beam is offset by a wavelength value of a Raman resonance of a specific molecular species from a wavelength of the beam from the second laser.

Additional features and advantages will be set forth in part in the description which follows, being apparent from the description of or learned by practice of the disclosed embodiments. The features and advantages will be realized and attained by means of the elements and combinations particularly pointed out in the appended claims.

It is to be understood that both the foregoing general description and the following detailed description are exemplary and explanatory only and are not restrictive of the scope of the embodiments, as claimed.

BRIEF DESCRIPTION OF THE DRAWINGS

The accompanying drawings, which are incorporated in and constitute a part of this specification, illustrate embodiments and, together with the description, serve to explain the features, advantages, and principles of the disclosed embodiments.

DETAILED DESCRIPTION

Figure 1:
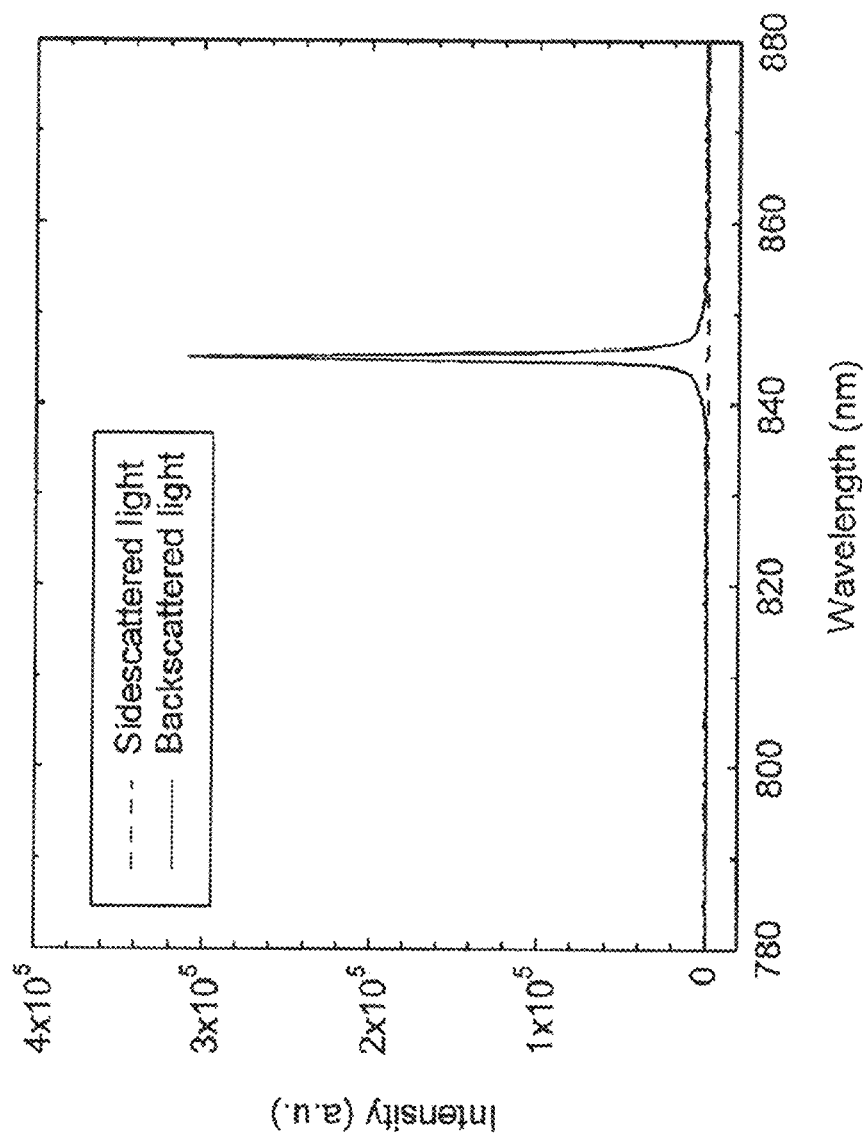
FIG. 1 depicts exemplary spectra of side-scattered light and back-scattered light for backward lasing from atomic oxygen in atmospheric pressure air.

Reference will now be made in detail to the one or more embodiments, characteristics of which are illustrated in the accompanying drawings. Wherever possible, the same reference numbers will be used throughout the drawings to refer to the same or like parts.

As used herein, "lasing" refers to amplified stimulated emission of radiation. For avoidance of doubt, and consistent with the disclosure, "lasing" as described herein does not require the use of mirrors.

Described herein is an air laser, the use of the air laser for remote detection, and a method for causing natural air to lase through the use of an excitation laser which can be tuned to a specific wavelength associated with oxygen or nitrogen.

Consistent with this disclosure, the air laser can be used for detection of molecular species in air through both linear and nonlinear processes involving either the forward propagating pump beam or the backward propagating air laser beam.

Furthermore, and consistent with this disclosure, no ionization or spark formation in air is required for the disclosed method and system for causing natural air to lase. The lasing can occur in both the forward and reverse directions relative to an excitation laser beam. The lasing can be in the near infrared corresponding to a region of high atmospheric transmission, and the excitation beam can also be in a region of atmospheric transmission. In this way, the lasing can be accomplished at long ranges from the source of an excitation laser. The reverse lasing feature can provide a laser beam that propagates back towards the excitation laser source. In that manner, the reverse propagating laser beam can provide a method for remote sampling of molecular species contained in the air through both Raman and four wave mixing interactions. It can also serve as an indicator of spatial, temporal, amplitude or polarization modulation of the pump laser beam caused by another forward propagating beam that co-propagates with and overlaps the beam from the pump laser such that it modulates the beam from the pump laser through interactions with selected molecular species. The reverse propagating air laser beam and the associated molecular signals can be separated from the excitation laser beam through the use of appropriate filters and dichroic mirrors.

In general, consistent with this disclosure, embodiments of an air laser can use the laser-induced dissociation of either nitrogen or oxygen into their atomic components—together with lasing from those atomic components—to create a lasing medium in air. The subsequent air laser can overcome limitations on detection signal strength by creating lasing in the backward direction in atmospheric pressure air. The backward-propagating laser beam can be used in optical detection methods and can lead to a backward propagating signal that can contain information relating to molecular species in the air. For example, and without limitation, the coherent nature of the backward-propagating laser beam can cause the light bearing any signal to be concentrated in a backward-directed beam, so that single-ended detection can be achieved. Moreover, and without limitation, this backward-propagating laser beam can participate in nonlinear interactions with other laser beams propagating in the forward direction in order to form back-directed nonlinear optical processes that can further enhance stand-off detection capabilities.

Consistent with this disclosure, and without limitation methods and systems for lasing in air can include the use of one or more lasers for the dissociation of oxygen or nitrogen molecules into atomic oxygen or nitrogen, and the excitation of that atomic oxygen or nitrogen by two photon absorption. In many cases the same laser can be used for both the dissociation of the molecular species and the excitation of the atomic species. In these circumstances, the pump laser can be tuned to the two-photon resonance associated with the atomic fragment. If the same wavelength interacts with the original molecular species such that dissociation occurs, then only one laser is necessary for the air lasing process to be achieved. Because the initial molecular species present in air can have many resonances associated with numerous rotational, vibrational and electronic single and multiphoton interactions, cases—such as those consistent with this disclosure—are likely to occur. When the population of the two-photon-excited state of the molecule becomes larger than the relevant lower atomic states, population inversion can occur along a path, and a subsequent gain along that path can be achieved due to the population inversion. The gain path can be in both the forward direction and the reverse direction along the excitation laser path, and can lead to laser beams propagating in both the forward direction and the reverse direction. Subsequently, the air laser beam in the reverse direction can be further amplified by optically pumping at least one of oxygen and nitrogen at sequential locations into appropriate excited states, and timing such optical pumping to coincide with the arrival of a backward propagating laser pulse.

Consistent with this disclosure, the detection of molecular species can be implemented according to several embodiments. By way of example only, and without limitation, stimulated Raman scattering effects can be utilized in one embodiment. In this embodiment, the forward-propagating and backward-propagating laser beams along the gain path can interact with molecules in the gain path, producing Raman-shifted sidebands whose wavelengths can be indicative of a specific molecular species present in the air.

In a further embodiment consistent with this disclosure, and because the excitation process can involve the absorption of two or more photons, an excitation laser beam can be configured to be well focused. Moreover, in an embodiment, phase correction techniques can be used to overcome issues associated with fluctuation in the air index of refraction. In these circumstances an adaptive optic deformable transmitting mirror can be used to modify the phase to compensate for atmospheric phase distortion. The amplitude of the return air laser beam can provide a highly sensitive measure of the pump laser focus, so when the return air laser beam amplitude is maximized, air distortion associated with propagation of the pump beam has been corrected.

An exemplary air laser, consistent with one embodiment, is described below. Where a molecular species in air includes molecular oxygen, a first laser consistent with this disclosure can include a 783.5 nm titanium sapphire laser and a 1064 nm Nd:YAG laser, where the 783.5 nm titanium sapphire laser is configured to generate a 100 psec laser pulse which can be upconverted by mixing with a 20 nanosecond long pulse from the 1064 nm Nd:YAG laser, and then doubling the subsequently generated 451.2 nm radiation to 225.6 nm—the 225.6 nm wavelength corresponding to the two photon $2^3P$-$3^3P$ transition in atomic oxygen. The first laser, configured to generate a 225.6 nm laser pulse, can serve to both dissociate the molecular oxygen into atomic oxygen, and to excite the atomic oxygen to an upper lasing state through resonant two-photon absorption. The first laser can be configured to focus into air with a 10 cm focal length lens, thereby producing a focal volume with a Rayleigh range (depth of focus) of less than 1 mm. The lasing transition associated with the air laser can be from the excited $3^3P$ state to a lower-lying $3^3S$ state of atomic oxygen at 844 nm, which lies in the near infrared.

Although the description above is directed to lasing in air, embodiments consistent with this disclosure can be directed to lasing of any molecular gas. Further still, although the above embodiment utilizes excited states accessible through two-photon absorption, embodiments consistent with this disclosure can also utilize excited states accessible through three-photon, four-photon, or higher photon absorption as appropriate (subject to the usual quantum mechanical transition rules, such as conservation of angular momentum). The lasing from the air laser can be observed in the backward propagating direction by splitting the infrared beam (which is from the air laser) from the forward propagating excitation laser beam (which can be from the first laser) using a dichroic mirror, and then passing the infrared beam into a detector such as a spectrometer. The fact that the transition is lasing can be confirmed by observing the ratio of the backward propagating light at 844.6 nm to the fluorescence at that same wavelength seen from the side of the excitation region. For example, the long and thin geometry of the excited region leads to gain along the length of the volume that far surpasses gain across the width of the volume.

In the absence of lasing, the fluorescence seen in either direction is expected to simply reflect the ratio of the sampled volumes—assuming the fluorescence is from an optically thin transition. In the presence of lasing, however, a signal from the long dimension far exceeds this value.

Amplified spontaneous emission from oxygen emission in air consistent with this disclosure is depicted in FIG. 1. In particular, backward lasing from atomic oxygen in atmospheric pressure air is shown. The large ratio of back-scattered emissions to side-scattered emissions is a characteristic of amplified stimulated emission and is a reliable indicator of lasing. The solid curve is the spectrum seen in the backward direction and the dotted line is the spectrum seen from the side. As depicted in FIG. 1, the amplitude of the backward lasing signal is more than six orders of magnitude greater than that seen from the side, far exceeding the sampled volume ratio. In addition, the divergence of the emitted backward beam is small, echoing the convergence of the pumping beam corrected for the difference in wavelength. Consistent with this disclosure, similar behavior can occur with molecular and atomic nitrogen (in place of molecular and atomic oxygen). In the case of nitrogen, however, an excitation laser wavelength can be set to excite a two-photon transition at 211 nm and the lasing can occur at 809 nm.

Consistent with this disclosure, a laser beam can be generated in room air pumped by a UV laser at 226 nm through two-photon excitation of atomic oxygen. An air laser beam can propagate both forward and backward. FIGS. 1-7 discussed herein depict details associated with a backward propagating air laser beam.

Consistent with this disclosure, and without limitation, optical pumping can also be accomplished using a laser at 452 nm by four photon excitation.

As discussed above, FIG. 1 depicts backscattered light at 844.6 nm, which corresponds to an atomic oxygen line. Furthermore, FIG. 1 depicts strong emission along the pump laser line (forward and backward) and no light detected sideways.

Figure 2:
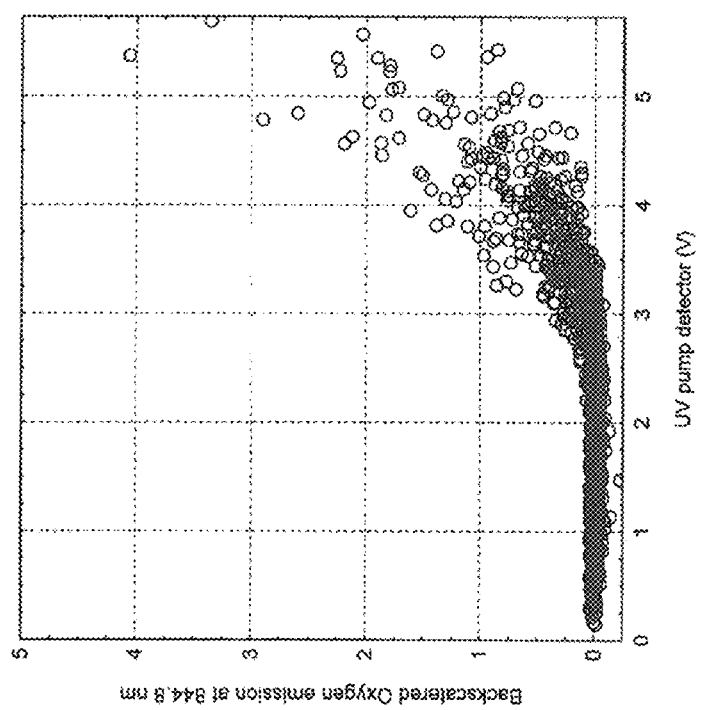
FIG. 2 depicts a linear scale portion of a plot of threshold and power dependence of back-scattered light consistent with this disclosure.
Figure 3:
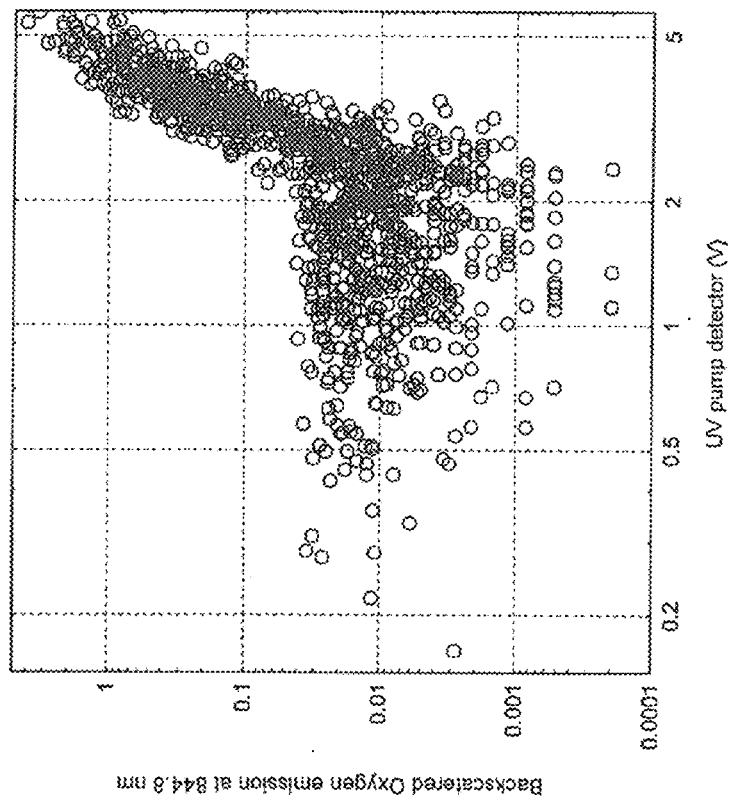
FIG. 3 depicts a log-log scale portion of a plot of threshold and power dependence of back-scattered light consistent with this disclosure.

FIGS. 2 and 3 depict, respectively, a linear scale portion of a plot of threshold and power dependence, and a log-log scale portion of a plot of threshold and power dependence. One of ordinary skill in the art should appreciate that threshold followed by highly nonlinear power dependence is a characteristic of lasing.

Figure 4:
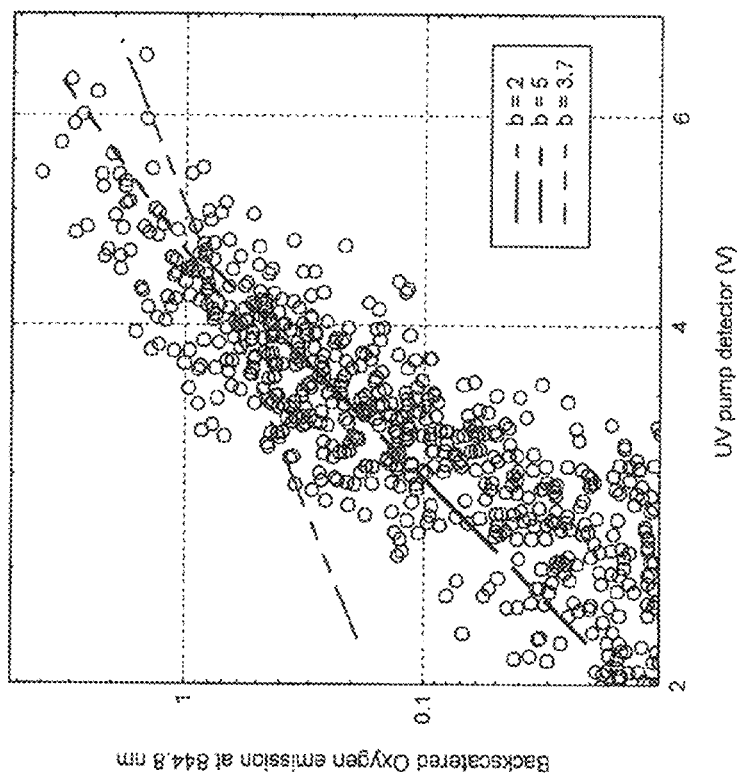
FIG. 4 depicts a portion of FIG. 3 with lines depicting various power-law dependencies.

FIG. 4 depicts a portion of FIG. 3 with lines depicting various power-law dependencies. As the power-law dependency ("b") is greater than 2 (i.e., b>2 in $I_{oxygen}=a\,(I_{UVpump})^b$), the depicted spectrum at 844.8 nm is not simply a function of two-photon laser induced fluorescence (being driven at 226 nm).

That is, two-photon excitation has square dependence (b=2) while lasing (amplified spontaneous emission) has a higher pump power dependence (b>2).

Figure 5:
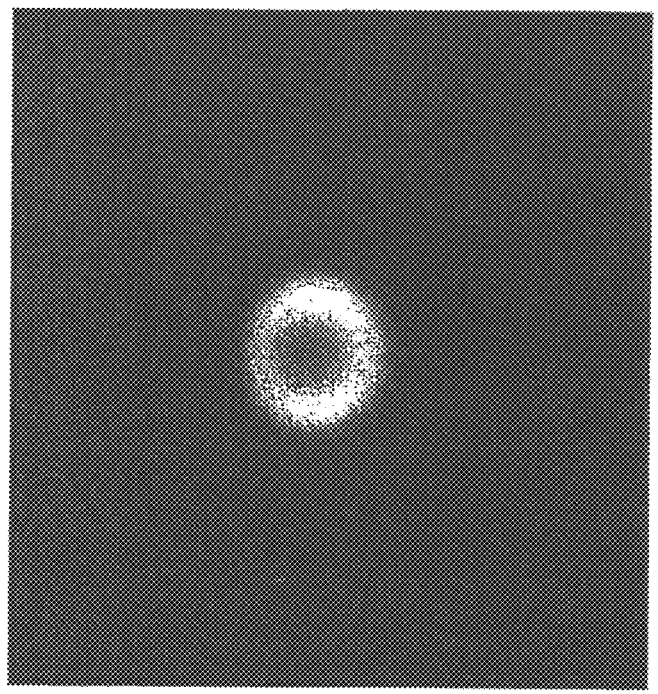
FIG. 5 is an exemplary photo of a beam divergence at an exemplary distance from a source of 25 cm.
Figure 6:
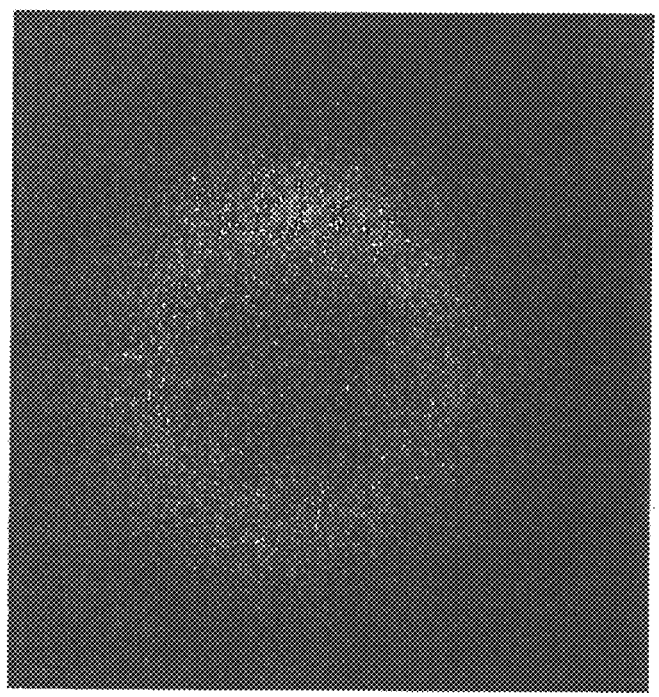
FIG. 6 is an exemplary photo of a beam divergence at a second exemplary distance from a source of 75 cm.

FIG. 5 depicts an example photograph of beam divergence at 25 cm with an oxygen emission beam size of 1.1 cm and an UV pump beam size of 3 mm. FIG. 6 depicts an example photograph of beam divergence at 75 cm with an oxygen emission beam size of 3.1 cm and an UV pump beam size of 9 mm. The depicted divergence is 4.7 degrees with an oxygen laser at 845 nm and 1.43 degrees with a pump laser at 226 nm, where: $\theta_{oxygen}/\theta_{UV}=3.3$ and $\lambda_{oxygen}/\lambda_{UV}=3.7$.

Figure 7:
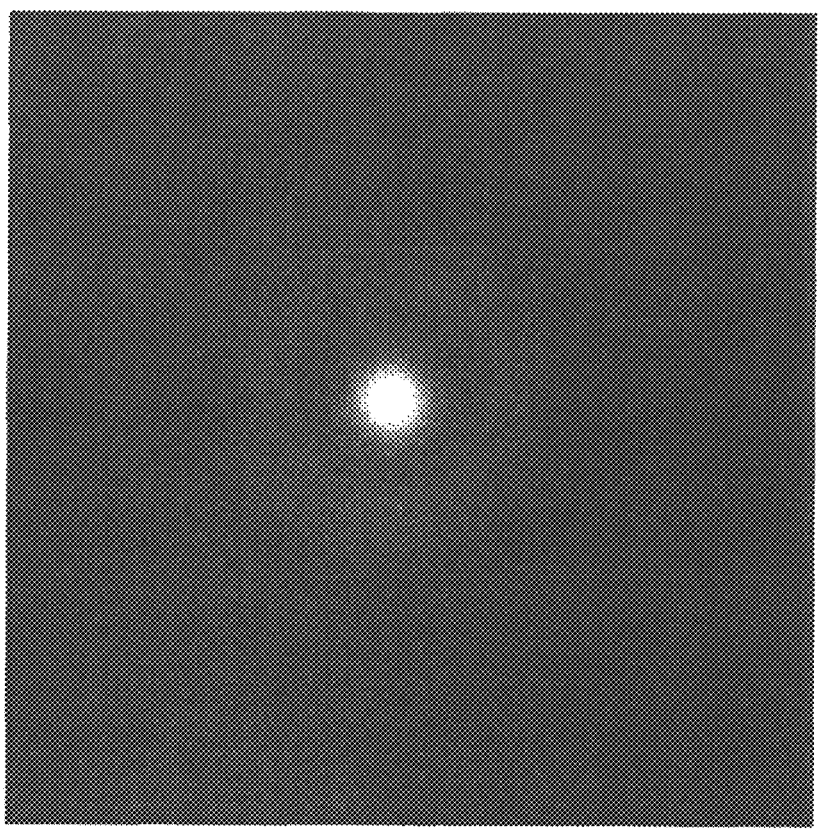
FIG. 7 is an exemplary photo of backward lasing from atomic oxygen in a methane/air flame.

FIG. 7 shows an example photograph of backward lasing from atomic oxygen in a methane/air flame. The donut mode seen in air is not seen from the atomic oxygen in a flame. Accordingly, the donut mode can be associated with the dissociation of molecular oxygen.

Consistent with this disclosure, the stand-off detection of trace molecular species at a distance in the atmosphere can be an important capability for pollution detection and for the detection of volatile indicators of explosives and other hazardous materials. As discussed herein, and without limitation, lasing can be achieved in atmospheric pressure air through the dissociation of molecular oxygen and the subsequent 226 nm two photon excitation of the atomic oxygen fragments. This lasing can occur along a focal region of the pumping 226 nm laser, and can lead to a near infrared laser beam at 845 nm propagating in both a forward direction and in a backward direction. In particular a backward propagating beam can come back along a path determined by the beam of the pump laser to the source location and can be separated from the oppositely propagating pump beam with a dichroic mirror. Consistent with this disclosure a backward lasing beam can be used for stand-off detection.

Figure 8:
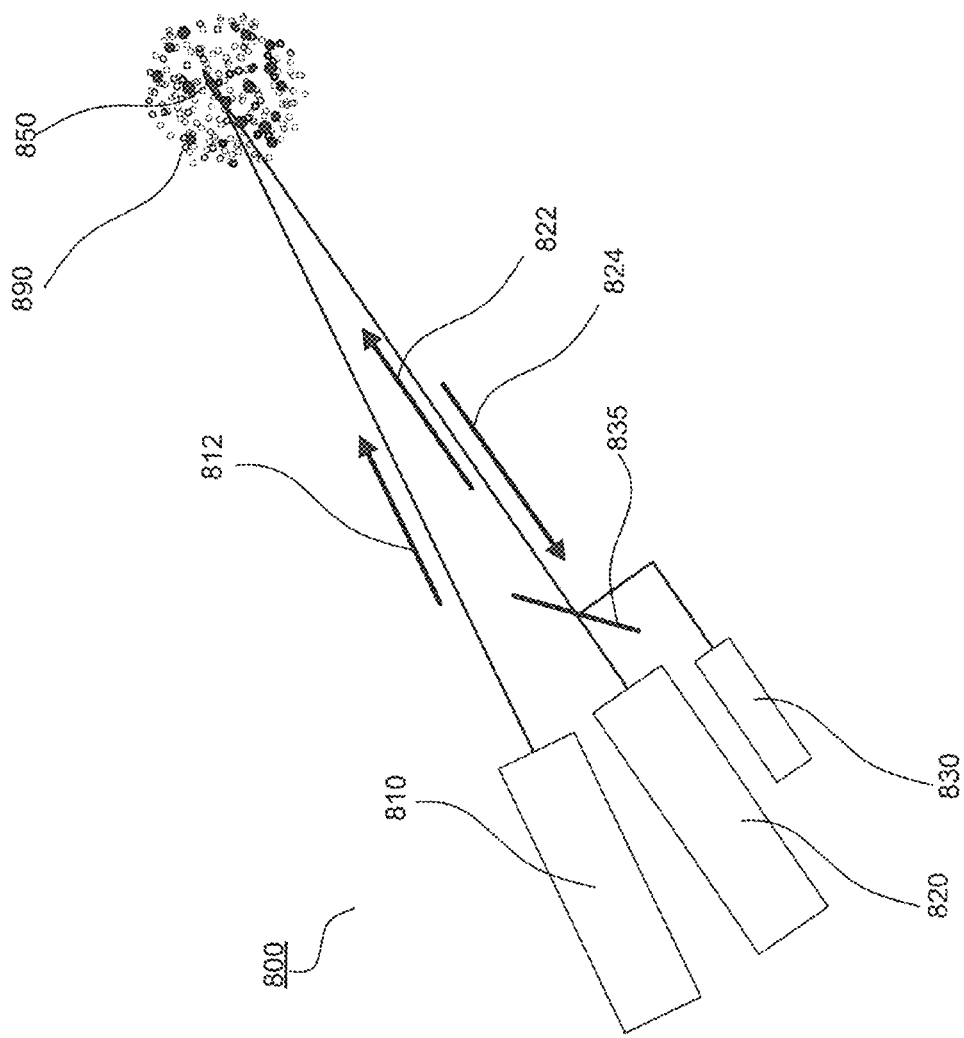
FIG. 8 is a schematic of a system for modulation of a pump laser beam by a modulating laser beam consistent with the disclosure.

Furthermore, the sensitivity of the amplitude and mode structure of a backward-generated air laser beam to the characteristics of the two-photon pump laser allows for a high sensitivity detection capability. For example, and as depicted in system 800 in FIG. 8, a modulation laser 810 that generates a beam (directed along arrow 812) configured to overlap and co-propagate with a beam originating from a two-photon pump laser 820 can be used to modulate the beam originating from the pump laser 820. System 800, consistent with this disclosure can then be configured to detect a modulation in the beam originating from the pump laser 820 (and directed along arrow 822) based upon a detected change in properties of the returning air laser beam (directed along arrow 824). As depicted in FIG. 8, mirror 835 can be used to separate the returning air laser beam and direct it towards photon detector 830. In one embodiment, by arranging for the modulation laser 810 to create the modulation in the beam originating from the two-photon pump laser 820 based upon an interaction with a specific molecular species that may be present in air 890, system 800 can be configured to determine whether that molecules species is present based upon a detected change in the properties of the returning air laser beam (i.e., the air laser beam return along direction 824).

Without limitation, and consistent with this disclosure, any small change in the energy fluence of the beam from the pump laser 820 (where energy fluence is in units of joules per unit area), where the beam from the pump laser 820 passes through a focal zone 850 can change the energy of an air laser beam as described herein. Changes in the mode and polarization of the pump laser 820 can change the mode structure and polarization of the air laser beam. Furthermore, and consistent with this disclosure, the polarization of the air laser beam is dependent upon the polarization of the beam from the pump laser 820. Changes in the pump laser wavelength can also lead to changes in both the air laser energy and the air laser mode. Note that laser 830 is depicted in system 800 of FIG. 8 to correspond to the source of a modulation laser beam that interacts with molecules present in air 890. As depicted in FIG. 8, the direction 812 of the beam from the laser 810 is co-propagating with direction 822 of the beam from the two-photon pump laser 820. Both beams are configured to converge at focal zone 850.

Figure 9:
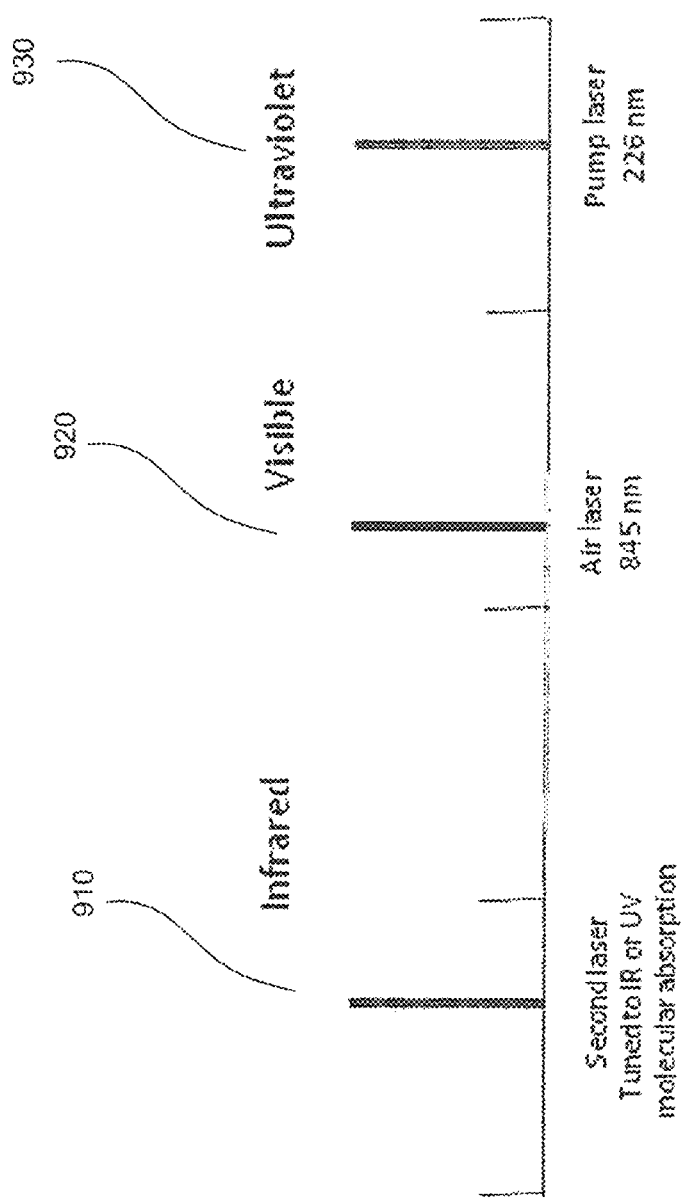
FIG. 9 depicts a relative frequency tuning value of a modulation laser relative to a pump laser and an air laser consistent with one aspect of this disclosure and the system of FIG. 8 (where wavelengths value are depicted)

Consistent with this disclosure, one method of detecting a specific molecular species can include causing a change in the index of refraction of the air 890. This can be achieved by heating the air 890 through absorption of energy from a co-propagating beam (originating from the modulation laser 810) by the specific molecule species of interest. Without limitation, the change of the index of refraction of the air 890 can be due to an associated variation of air density. This energy absorption by the specific molecular species can be into any internal mode of the molecule in the species—including rotational, vibrational or electronic modes. FIG. 9 depicts an exemplary tuning frequency of a modulation laser 810 tuned to a molecular absorption frequency (i.e., wavelength 910) in the infrared associated with a specific molecular species. Consistent with this disclosure, the change in the index of refraction of air 890 change can lead to a change of the focusing properties of the beam from the two-photon pump laser 820, and thus a change in the properties of the returning air laser beam (at wavelength 920). The overlap of the beam from the modulation laser 810 with the beam from the pump laser 820 (at wavelength 930) can be optimized in time and space to produce a maximal change in the focal properties of the beam from the two-photon pump laser 820, and thus a maximal change in properties of a returning air laser beam. Heating can also be achieved with a pulse-shaped femtosecond laser optimized for thermal interactions with a selected molecule.

Figure 10:
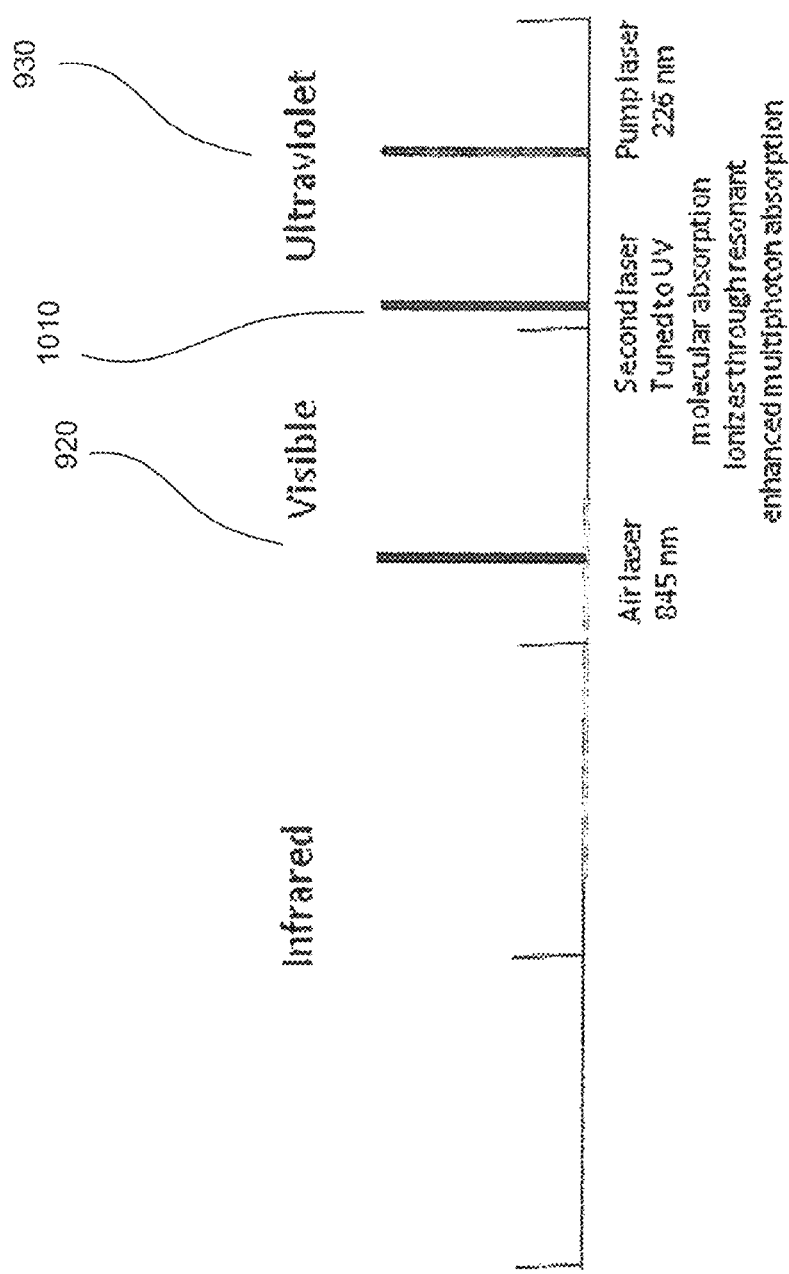
FIG. 10 depicts a relative frequency tuning value of a modulation laser relative to a pump laser and an air laser consistent with another aspect of this disclosure and the system of FIG. 8 (where wavelengths value are depicted)

Another embodiment consistent with this disclosure can include causing a change in the index of refraction of the air 890 through multi-photon absorption of a beam from the modulation laser 810, leading to ionization of a molecular species of interest. FIG. 10 depicts the frequency of the modulation laser 810 tuned to an ultraviolet transition (at wavelength 1010) leading to ionization through resonant multi-photon ionization. Consistent with this application, such targeted ionization can lead to a change in the index of refraction of the air 890 through the presence of free electrons and ions. Consistent with this disclosure, the change in the index of refraction of air 890 can lead to a change of the focusing of the two photon pump laser 820 and thus a change in the properties of the returning air laser beam. Ionization may also be achieved with a pulse shaped femtosecond laser optimized to ionize the selected molecule.

Figure 11:
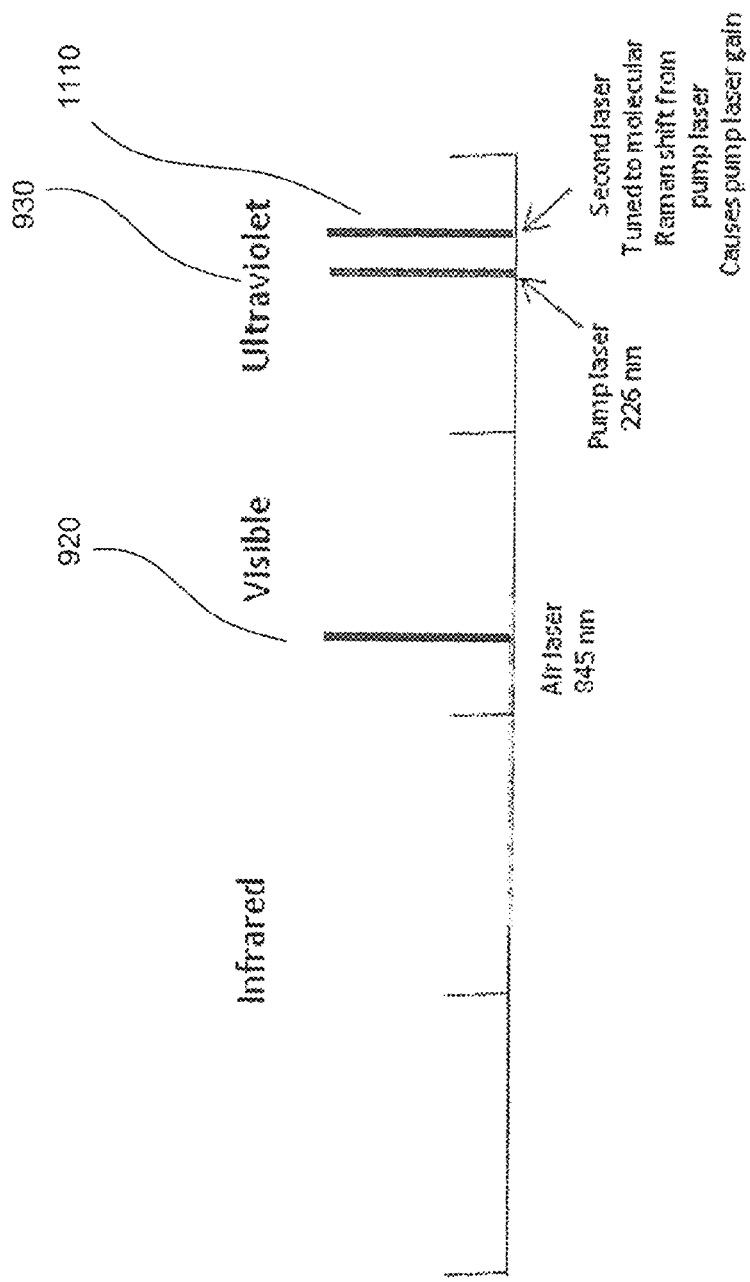
FIG. 11 depicts a relative frequency tuning value of a modulation laser relative to a pump laser and an air laser consistent with yet another aspect of this disclosure and the system of FIG. 8 (where wavelengths value are depicted)

A further embodiment consistent with this disclosure can include causing a change in the amplitude of the two-photon pump laser 820 through a stimulated Raman interaction with a beam from the modulation laser 810, where the two-photon pump laser 820 can be either amplified or attenuated through a nonlinear interaction with a selected molecular species. FIG. 11 depicts a frequency of the modulation laser 810 tuned to a higher frequency (i.e., a shorter wavelength 1110) corresponding to a Raman shift from the pump laser 820 wavelength of a molecule of interest. In this embodiment, the beam from the modulation laser 810 can be tuned such that it is offset in frequency by an appropriate molecular Raman resonance from the two-photon pump laser 820. The Raman interaction can lead to a gain in the beam from the two-photon pump laser 820. The associated change in the fluence of the beam from the pump laser 820 can further cause a change in the returning air laser beam.

Figure 12:
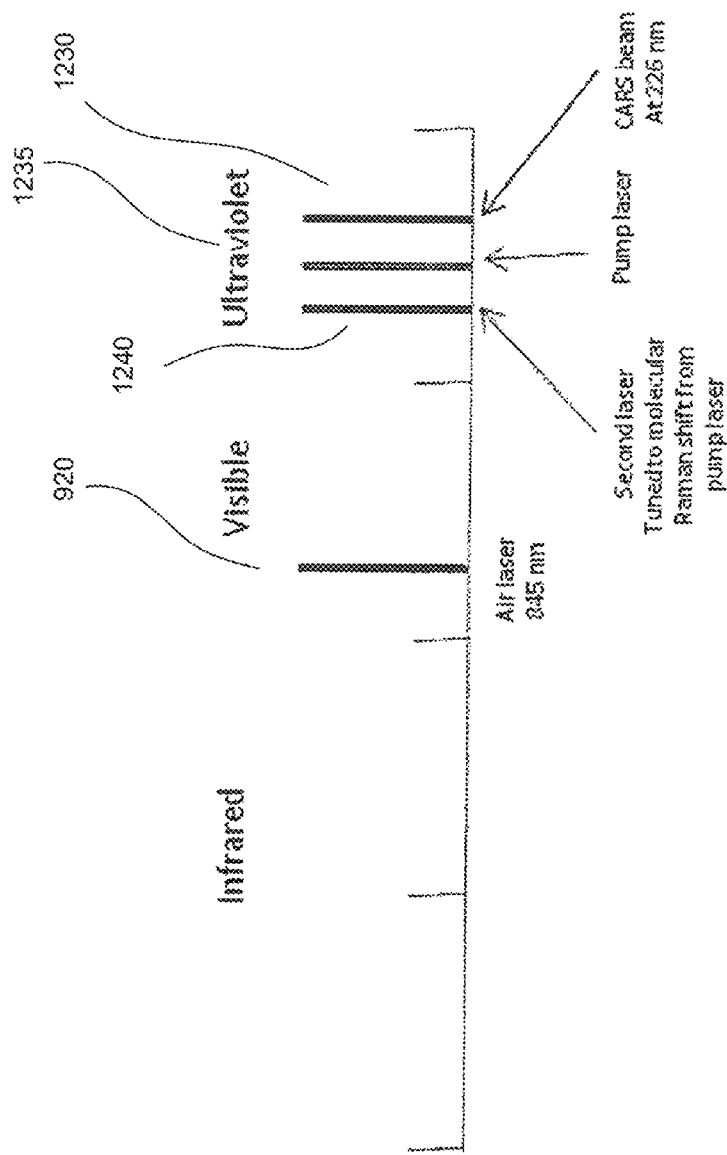
FIG. 12 depicts a relative frequency tuning value of a modulation laser relative to a pump laser and an air laser consistent with a further aspect of this disclosure and the system of FIG. 8 (where wavelengths value are depicted)

Further still, an embodiment consistent with this disclosure can include causing the formation of a second forward propagating two-photon pump beam through a nonlinear interaction of a beam from a first laser (such as laser 820 in system 800) and a beam from the modulation laser 810. In this application, and without limitation, a nonlinear interaction between the beam from the first laser and the beam from the modulation laser 810 can generate a second two-photon pump beam at a driving frequency, where the second two-photon pump beam drives the backward propagating air laser beam. The system can be configured so that the second two-photon pump beam is generated only when the appropriate molecular species is present such that the first beam and the beam from the modulation laser 810 interact to form the second two-photon pump beam. Thus in the absence of the interaction, there is no return air laser beam created, but in the presence of the interaction, a return air laser beam is created. For example the two co-propagating lasers (i.e., the first beam and the beam from the modulation laser 810) can be separated in frequency by a characteristic Stokes frequency shift of a selected molecule of interest, causing the formation of an anti-Stokes beam which is at the two photon laser frequency through a Coherent Anti-Stokes Raman interaction. FIG. 12 depicts a frequency (at wavelength 1240) of the modulation laser 810 tuned to a molecular Raman shift, a frequency (at wavelength 1235) of the first laser beam (which is not at the frequency necessary to drive the backward propagating air laser beam), and a frequency (at wavelength 1230) of a resulting CARS beam. In the case of an air laser based on the transitions available in molecular and atomic oxygen, the wavelength of the resulting CARS beam is at 226 nm.

In a further embodiment consistent with this disclosure, a system and/or method can include causing a change in the polarization of the beam from the pump laser 820 through a nonlinear interaction with the beam from the modulation laser 810. This, for example, can be configured to occur with a nonlinear Kerr-type or stimulated Raman interaction using an orthogonal or rotational polarized modulation laser that modulates a selected molecular species in such a manner as to change the polarization of the beam from the two-photon pump laser 820. In this embodiment, the polarization of the returning air laser can be monitored with a polarizer.

Further embodiments consistent with this disclosure can include the use of any other system and/or process that can cause a change in the amplitude, polarization, frequency, mode structure or temporal behavior of a beam pumping the air laser, leading to either the creation of the air laser or a change in its properties that can be detected in the backward propagating beam.

Further still, and consistent with embodiments of this disclosure, the modulation of the return air laser beam as a result of changes in the properties can be detected in relation to a return air laser beam generated in the absence of modulation. The return air laser beam without modulation can act as a reference beam. Because, in some embodiments, the air laser beam can be formed by pulses of the pump laser with short time duration, a system consistent with this disclosure can be configured to detect a modulated return air laser beam on a pulse-by-pulse basis. Moreover, the natural variation of pump laser focus as a result of pulse-to-pulse variations in pump laser energy, temporal structure and mode, and as a result of non-uniformities in the air along the propagation path, certain embodiments can be configured to allow for a substantially simultaneous pulse reference. This can be achieved by splitting the pump laser into two beams and sending both out to focal points that are closely separated, as shown in system 1300 depicted in FIG. 13. In this configuration, a beam from a two-photon pump laser 820 is split into two beams. A modulation laser 810 generates a modulation laser beam (directed along arrow 812) that is configured to overlap with one of the split beams from the two-photon pump laser 820. The second of the two split beams is a beam (along direction 1322) is configured to be separate from the beam of modulation laser 810. Using the system 1300, a pulse-to-pulse reference can be generated in the return path from each of the split beams. The returning air laser beam (along direction 1324) that does not involve an interaction with the beam from the modulation laser 810 can act as the reference and can be directed toward photodetector 1330. The other returning air laser beam (along direction 824) can be configured to be a function of the modulation described above and can be directed toward photodetector 830.

Figure 13:
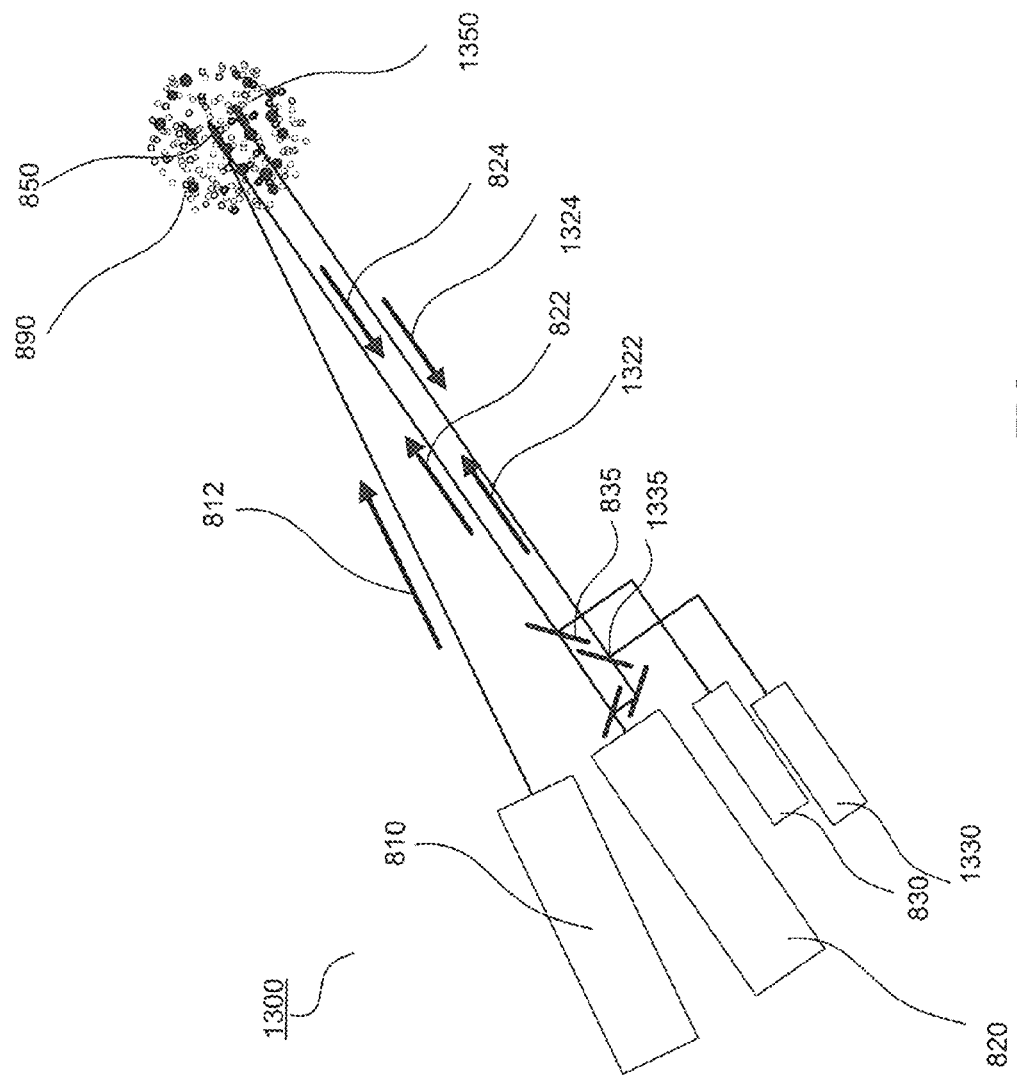
FIG. 13 is a schematic of a modulation of a pump laser beam by a modulating laser beam and a reference air laser beam that is not modulated by the modulating laser beam consistent with the disclosure.

In one embodiment consistent with FIG. 13, the modulation laser 810 can be switched on and off with alternate pulses from the pump laser 820, and the signals from the two returning air laser beams can be compared as a function of this modulation. This approach can both suppress any effects associated with pulse-to-pulse fluctuations in the beam of the pump laser 820, and minimize any atmospheric effects—as both beams can be configured to pass through closely adjacent regions of the atmosphere. Consistent with an embodiment, a separation in focal zones (850 and 1350) can be just a few millimeter—so that it is large enough to allow the beam from the modulation laser 810 to uniquely overlap one of the focal zones and not the other and also large enough to provide enough separation between the air laser beams so that the returning air laser beams can be separately distinguished. There can also include applications where the beam of the modulation laser 810 overlaps both split beams of the two-photon pump laser 820, thereby maximizing the differential in the air lasers created by both.

Other embodiments will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for lasing in air without a resonating cavity, the method comprising:
   using a source of laser pulses to dissociate at least one molecular species comprising atomic constituents into the atomic constituents; and
   using the source of laser pulses to excite at least one of the dissociated atomic constituents by at least two-photon absorption to an energy level that forms a population inversion along an excitation path of an upper lasing level to produce a gain path for amplified stimulated emission of radiation.

2. The method of claim 1, wherein the source of laser pulses comprises a first laser and a second laser, the first laser configured to generate a first laser pulse to dissociate the at least one molecular species, and the second laser configured to generate a second laser pulse to excite the at least one of the dissociated atomic constituents.

3. The method of claim 1, wherein the source of laser pulses comprises a laser configured to generate a plurality of laser pulses, each laser pulse interacting with both the at least one molecular species and the at least one dissociated atomic constituent, the interaction with the at least one molecular species dissociating the at least one molecular species and the interaction with the at least one dissociated atomic constituent exciting the at least one dissociated atomic constituent.

4. The method of claim 1, wherein the at least one molecular species is selected from the set of: molecular oxygen and molecular nitrogen.

5. The method of claim 1, wherein the gain path is in both a forward direction and a reverse direction along the excitation path, leading to air laser beams propagating in both the forward direction and the reverse direction.

6. The method of claim 5, wherein the air laser beam propagating in the reverse direction is amplified by subsequent dissociation and pumping of at least one of the atomic constituents at a location and a time coinciding with a backward propagating air laser pulse.

7. The method of claim 1, further comprising detecting a specific molecular species.

8. A method of detecting molecular species in air, the method comprising:
using a source of laser pulses to dissociate at least one molecular species comprising atomic constituents into the atomic constituents;
using the source of laser pulses to excite at least one of the dissociated atomic constituents by at least two photon absorption to form a population inversion along an excitation path of an upper lasing level to produce a gain path for amplified stimulated emission of radiation for lasing in air without a resonating cavity; and
employing stimulated Raman scattering effects;
wherein the gain path is in both a forward direction and in a reverse direction along the excitation path, leading to air laser beams propagating in both the forward direction and the reverse direction;
wherein at least one air laser beam interacts with a specific molecular species in the excitation laser path, the interaction producing Raman shifted sidebands comprising wavelengths; and
wherein the wavelengths are indicative of the specific molecular species.

9. The method of claim 8, wherein the source of laser pulses comprises a first laser and a second laser, the first laser configured to generate a first laser pulse to dissociate the at least one molecular species, and the second laser configured to generate a second laser pulse to excite the at least one of the dissociated atomic constituents.

10. The method of claim 8, wherein the source of laser pulses comprises a laser configured to generate a plurality of laser pulses, each laser pulse interacting with both the at least one molecular species and the at least one dissociated atomic constituent, the interaction with the at least one molecular species dissociating the at least one molecular species and the interaction with the at least one dissociated atomic constituent exciting the at least one dissociated atomic constituent.

11. The method of claim 8, wherein the at least one molecular species is selected from the set of: molecular oxygen and molecular nitrogen.

12. A system for lasing a molecular gas in air without a resonating cavity comprising:
a source of laser pulses configured to dissociate at least one molecular species comprising atomic constituents into the atomic constituents;
wherein the source of laser pulses is also configured to excite at least one of the dissociated atomic constituents by at least two-photon absorption to form a population inversion along an excitation path of an upper lasing level to produce a gain path for amplified stimulated emission of radiation.

13. The system of claim 12, wherein the source of laser pulses comprises a first laser and a second laser, the first laser configured to generate a first laser pulse to dissociate the at least one molecular species, and the second laser configured to generate a second laser pulse to excite the at least one of the dissociated atomic constituents.

14. The system of claim 12, wherein the source of laser pulses comprises a laser configured to generate a plurality of laser pulses, each laser pulse interacting with both the at least one molecular species and the at least one dissociated atomic constituent, the interaction with the at least one molecular species dissociating the at least one molecular species and the interaction with the at least one dissociated atomic constituent exciting the at least one dissociated atomic constituent.

15. The system of claim 12, wherein the at least one molecular species is selected from the set of: molecular oxygen and molecular nitrogen.

16. The system of claim 12, wherein the gain path is in both a forward direction and a reverse direction along the excitation path, leading to air laser beams propagating in both the forward direction and the reverse direction.

17. The system of claim 16, wherein the air laser beam propagating in the reverse direction is amplified by subsequent dissociation and pumping of at least one of the atomic constituents at a location and a time coinciding with a backward propagating laser pulse.

18. A method of detecting molecular species in air, the method comprising:
using a source of laser pulses to dissociate at least one molecular species comprising atomic constituents into the atomic constituents;
using the source of laser pulses to excite at least one of the dissociated atomic constituents by at least two-photon absorption to form a population inversion along an excitation path of an upper lasing level to produce a gain path for amplified stimulated emission of radiation for lasing in air without a resonating cavity;
using a modulation laser to generate a modulation beam configured to co-propagate with a beam from the source of laser pulses along the excitation path; and
determining whether the co-propagating modulation beam alters a property of a reverse-propagating air laser beam;
wherein the gain path is at least in a reverse direction along the excitation path, leading to the reverse-propagating air laser beam;
wherein the modulation beam is configured to transfer energy to a specific molecular species such that the energized specific molecular species alters an index of refraction of air in the excitation laser path.

19. The method of claim 18, wherein the source of laser pulses comprises a first laser and a second laser, the first laser configured to generate a first laser pulse to dissociate the at least one molecular species, and the second laser configured to generate a second laser pulse to excite the at least one of the dissociated atomic constituents.

20. The method of claim 18, wherein the source of laser pulses comprises a laser configured to generate a plurality of laser pulses, each laser pulse interacting with both the at least one molecular species and the at least one dissociated atomic constituent, the interaction with the at least one molecular species dissociating the at least one molecular species and the interaction with the at least one dissociated atomic constituent exciting the at least one dissociated atomic constituent.

21. The method of claim 18, wherein the at least one molecular species is selected from the set of: molecular oxygen and molecular nitrogen.

22. The method of claim 18, wherein the modulation beam is configured to heat the specific molecular species.

23. The method of claim 18, wherein the modulation beam is configured to ionize the specific molecular species.

24. The method of claim 18, wherein determining whether the co-propagating modulation beam alters a property of the reverse-propagating air laser beam includes using the source of laser pulses to form a second excitation path of the upper lasing level to produce a second gain path for amplified stimulated emission of radiation in the backward direction relative to the source of laser pulses, thereby providing a reference reverse-propagating air laser beam.

25. A system for detecting molecular species in air, the system comprising:

a source of laser pulses configured to dissociate at least one molecular species comprising atomic constituents into the atomic constituents, the source of laser pulses further configured to excite at least one of the dissociated atomic constituents by at least two photon absorption to form a population inversion along an excitation path of an upper lasing level to produce a gain path for amplified stimulated emission of radiation for lasing in air without a resonating cavity; and a modulation laser configured to generate a modulation beam, the modulation beam configured to co-propagate with a beam from the source of laser pulses along the excitation path;

wherein the gain path is at least in a reverse direction along the excitation path, leading to a reverse-propagating air laser beam;

wherein the modulation beam is configured to transfer energy to a specific molecular species such that the energized specific molecular species alters an index of refraction of air in the excitation laser path.

26. The system of claim 25, wherein the source of laser pulses comprises a first laser and a second laser, the first laser configured to generate a first laser pulse to dissociate the at least one molecular species, and the second laser configured to generate a second laser pulse to excite the at least one of the dissociated atomic constituents.

27. The system of claim 25, wherein the source of laser pulses comprises a laser configured to generate a plurality of laser pulses, each laser pulse interacting with both the at least one molecular species and the at least one dissociated atomic constituent, the interaction with the at least one molecular species dissociating the at least one molecular species and the interaction with the at least one dissociated atomic constituent exciting the at least one dissociated atomic constituent.

28. The system of claim 25, wherein the at least one molecular species is selected from the set of: molecular oxygen and molecular nitrogen.

29. The system of claim 25, wherein the modulation beam is configured to heat the specific molecular species.

30. The system of claim 25, wherein the modulation beam is configured to ionize the specific molecular species.

31. The system of claim 25, wherein the source of laser pulses is configured to form the population inversion along a second excitation path of the upper lasing level to produce a second gain path for amplified stimulated emission of radiation in the backward direction relative to the source of laser pulses, thereby providing a reference reverse-propagating air laser beam.

32. A method of detecting molecular species in air, the method comprising:
using a source of laser pulses to dissociate at least one molecular species comprising atomic constituents into the atomic constituents;
using the source of laser pulses to excite at least one of the dissociated atomic constituents by at least two photon absorption to form a population inversion along an excitation path of an upper lasing level to produce a gain path for amplified stimulated emission of radiation for lasing in air without a resonating cavity;
using a modulation laser to generate a modulation beam configured to co-propagate with a beam from the source of laser pulses along the excitation path; and
determining whether the co-propagating modulation beam alters a property of a reverse-propagating air laser beam;

wherein the gain path is at least in a reverse direction along the excitation path, leading to the reverse-propagating air laser beam;

wherein the modulation beam is configured to alter the amplitude of the beam from the second laser through a stimulated Raman interaction, wherein a wavelength of the modulation beam is offset by a wavelength value of a Raman resonance of a specific molecular species from a wavelength of the beam from the second laser.

33. The method of claim 32, wherein the source of laser pulses comprises a first laser and a second laser, the first laser configured to generate a first laser pulse to dissociate the at least one molecular species, and the second laser configured to generate a second laser pulse to excite the at least one of the dissociated atomic constituents.

34. The method of claim 32, wherein the source of laser pulses comprises a laser configured to generate a plurality of laser pulses, each laser pulse interacting with both the at least one molecular species and the at least one dissociated atomic constituent, the interaction with the at least one molecular species dissociating the at least one molecular species and the interaction with the at least one dissociated atomic constituent exciting the at least one dissociated atomic constituent.

35. A system for detecting molecular species in air, the system comprising:
a source of laser pulses configured to dissociate at least one molecular species comprising atomic constituents into the atomic constituents, the source of laser pulses further configured to excite at least one of the dissociated atomic constituents by at least two photon absorption to form a population inversion along an excitation path of an upper lasing level to produce a gain path for amplified stimulated emission of radiation for lasing in air without a resonating cavity; and
a modulation laser configured to generate a modulation beam, the modulation beam configured to co-propagate with a beam from the second laser along the excitation path;
wherein the gain path is at least in a reverse direction along the excitation path, leading to a reverse-propagating air laser beam;
wherein the modulation beam is configured to alter the amplitude of the beam from the source of laser pulses through a stimulated Raman interaction, wherein a wavelength of the modulation beam is offset by a wavelength value of a Raman resonance of a specific molecular species from a wavelength of the beam from the source of laser pulses.

36. The system of claim 35, wherein the source of laser pulses comprises a first laser and a second laser, the first laser configured to generate a first laser pulse to dissociate the at least one molecular species, and the second laser configured to generate a second laser pulse to excite the at least one of the dissociated atomic constituents.

37. The system of claim 35, wherein the source of laser pulses comprises a laser configured to generate a plurality of laser pulses, each laser pulse interacting with both the at least one molecular species and the at least one dissociated atomic constituent, the interaction with the at least one molecular species dissociating the at least one molecular species and the interaction with the at least one dissociated atomic constituent exciting the at least one dissociated atomic constituent.

* * * * *